United States Patent [19]

Fieseler et al.

[11] Patent Number: 4,698,976
[45] Date of Patent: Oct. 13, 1987

[54] DEVICE FOR PRODUCING A COLD TREATMENT GAS

[75] Inventors: Heinrich Fieseler, Dormagen; Klemens Thoma, Krefeld-Huls, both of Fed. Rep. of Germany

[73] Assignee: Messer Griesheim GmbH, Fed. Rep. of Germany

[21] Appl. No.: 839,188

[22] Filed: Mar. 13, 1986

[30] Foreign Application Priority Data

May 22, 1985 [DE] Fed. Rep. of Germany ... 8514989[U]

[51] Int. Cl.⁴ .............................................. F17C 11/00
[52] U.S. Cl. ........................................ 62/48; 62/50; 62/93; 62/514 R; 165/36
[58] Field of Search ............. 62/50, 51, 52, 53, 514 R, 62/48, 93; 165/34, 35, 36

[56] References Cited

U.S. PATENT DOCUMENTS

| 2,242,108 | 5/1941 | Bullowa et al. | 62/50 |
| 2,359,219 | 9/1944 | Jones | 62/52 |
| 2,760,342 | 8/1956 | Morrison | 62/50 |
| 3,058,317 | 10/1962 | Putman | 62/52 |
| 3,082,690 | 3/1963 | Reynolds et al. | 62/53 |
| 3,106,070 | 10/1963 | Harper et al. | 62/52 |
| 3,121,999 | 2/1964 | Kasbohm et al. | 62/50 |
| 3,304,730 | 2/1967 | Gorham | 62/53 |
| 3,421,574 | 1/1969 | Kals | 62/52 |
| 3,431,742 | 3/1969 | Green | 62/52 |
| 3,564,861 | 2/1971 | Anderson et al. | 62/50 |
| 3,591,962 | 7/1971 | Connell | 62/52 |
| 3,727,651 | 4/1973 | Biever | 62/52 |
| 3,791,351 | 2/1974 | Kent | 165/34 |
| 3,823,568 | 7/1974 | Bijasiewicz et al. | 62/52 |
| 4,015,436 | 4/1977 | Seki | 62/50 |
| 4,532,779 | 8/1985 | von der Bay et al. | 62/514 R |

FOREIGN PATENT DOCUMENTS 3242881 5/1984 Fed. Rep. of Germany .

Primary Examiner—Ronald C. Capossela
Attorney, Agent, or Firm—Connolly & Hutz

[57] ABSTRACT

A device is provided for producing a cold treatment gas from nitrogen and air for the cryotherapy of rheumatic diseases in which liquid nitrogen vaporizes and is mixed in the desired ratio with the dry air which is at a higher pressure. The device includes a vessel for the storage of the liquid nitrogen which has a capacity for carrying out at least one or more treatments. Heat exchanging apparatuses are installed in the vessel for channeling a portion of the air which is at a higher pressure. A blending intersection for blending vaporized nitrogen, cooled air and non-cooled air is attached to the vessel. A blower is provided with a dryer having an outlet pipe which branches to a connection with the blending intersection and to a connection with the heat exchanging apparatus.

10 Claims, 1 Drawing Figure

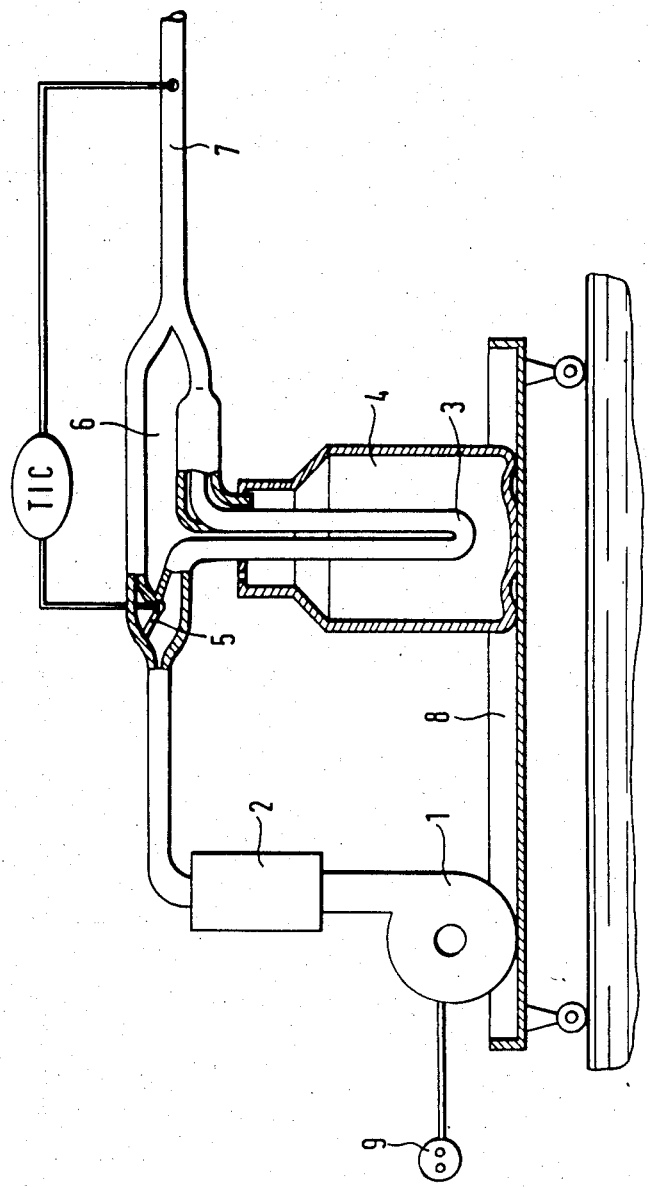

DEVICE FOR PRODUCING A COLD TREATMENT GAS

BACKGROUND OF THE INVENTION

Many devices are used for the cryotherapy of rheumatic diseases according to which the cold treatment gas is obtained by vaporizing liquid nitrogen. Air, which is mixed with the vaporized nitrogen, is used for heat exchange. Such devices, as for example, known from German patent publication Nos. 32 42 881 and 33 05 434, are suited for hospitals or therapy centers where a large number of treatment are planned.

These large devices require a quite high surveillance and safety expense. Thus, the oxygen content of the treatment room must be monitored since, in the case of sparse ventilation, it could drop to an unacceptable value. It must be assured that no air can condense in the storage vessel for liquid nitrogen. Concentrations of oxygen could hereby form in the liquid nitrogen from which (oxygen concentrations), after subsequent vaporization, explosive gas mixtures could result. Aside from this, effective installations for drying the air or the treatment gas are required since moisture which has frozen may not come in contact with the part of the body to be treated. These devices are therefore less suitable for normal medical practices where a treatment is only occasionally performed.

SUMMARY OF THE INVENTION

The object of the invention is therefore to achieve a device for cryotherapy which is suitable for normal medical practices and which requires only a small expense for surveillance.

The invention is based upon the idea of making the storage vessel for liquid nitrogen so small that only one or a few treatments can be carried out with the stored amount of nitrogen. It must, for all intensive purposes, be filled for every treatment from a customarily larger vessel for the safekeeping of liquid nitrogen. The stored nitrogen is either completely or, for the most part, consumed for the treatment.

The unused liquid nitrogen can subsequently eventually vaporize as a result of the natural incidence of heat. Because of the small amount of vaporized nitrogen which can possibly occur here, one can waive an oxygen surveillance since, in no case, can the oxygen content sink below an acceptable level. Since the contents of the vessel vaporize totally after each treatment, there is also no danger of an unacceptable oxygen buildup. This danger is further reduced by the fact that the air which serves to vaporize the liquid nitrogen does not come in direct contact with the liquid nitrogen.

Corresponding to the small amounts of nitrogen, only small amounts of air are needed. The air can be supplied by a small blower which, along with the vessel for liquid nitrogen is preferably firmly installed on a cart so that the device can be easily brought to the required location and be put away again. The drying of the air is also not a problem because of the small amount of treatment gas. Adsorption dryers or molecular sieves can be used for this. The moisture in the air can also be condensed out in a heat exchanger. An adsorption dryer can, for example, be traversed by the vaporized nitrogen during the subsequent idle period and regenerated.

THE DRAWING

The single FIGURE drawing illustrates an embodiment of the invention in schematic form.

DETAILED DESCRIPTION

The device illustrated in the drawing consists of two essential components, namely, the blower 1 with the dryer 2 hooked up behind it and the heat exchanging apparatus 3 in the vessel 4 for liquid nitrogen. Both of these components are connected with one another via a blending intersection 6. The blending intersection 6 has, at its inlet, an adjustable damper 5, through which the stream of concentrated air coming from the blower 1 is divided into two partial streams. The one partial stream flows through the heat exchanging apparatus 3, as a result of which liquid nitrogen is vaporized. The vaporized nitrogen blends with this partial stream in the blending intersection 6 in which the second stream of non-cooled air is also blended in again. The finished cold treatment gas of nitrogen and air is then available at the outlet pipe 7. The temperature of the treatment gas is measured and regulated. The regulation is carried out by actuating the adjustable damper 5, as a result of which action the portion of the concentrated air flowing through the heat exchanging apparatus 3 is increased or decreased. The amount of vaporized nitrogen varies accordingly. The entire installation is installed on a cart 8. It require only a simple electrical plug 9 in order to put it in operation.

The vessel 4 is filled with liquid nitrogen before putting the device in operation. At the end of the treatment, there is in the vessel 4, a residual amount of liquid nitrogen which gradually vaporizes due to heat incidence. This vaporized nitrogen can be used to regenerate the dryer 2 or to remove moisture which has condensed out there.

The typical method of operation of the invention's device which consists of filling the vessel 4 with liquid nitrogen before each treatment is, in itself, not economical since the vessel 4 and the blending intersection 6 with the outlet pipe 7 must be cooled to a low temperature each time. The losses which result are small, however, since the masses to be cooled are small. On the other hand, there is the far-reaching advantage that surveillance and control apparatuses can be omitted. Because of the small contents of the vessel 4, there is no danger of an unacceptable concentration of oxygen in the air in the room during treatments. An oxygen measuring device can thus be omitted. Since the piping system of the heat exchanging apparatus 3 is sealed or enclosed no oxygen buildup can result in the liquid nitrogen. It is additionally possible to vary the magnitude of the air stream fed by the blower 1 in order to make it suitable for various treatment requirements. Insofar as, during cold application, only single treatments are carried out and the treatment device must be cooled anew each time, the pipe act as condensation surfaces onto which moisture can deposit. If, for medical reasons, the application of a dry cold gas stream is indispensable, the connection of a dryer, e.g. molecular sieve, ahead of it is possible.

Besides cryotherapy in the field of medicine, other applications in technical disciplines are also conceivable, in which the device can be included over longer periods of operation. Condensed out moisture from the air, would in these cases, not be detrimental to the application. Such applications are, for example, the use in experiments involving freezing, the cooling of testing chambers or climate chambers where a cold temperature must be maintained, for example, for testing component part, or the cooling of surfaces.

As an alternative to the temperature regulation by feeding warm air via an adjustable damper 5, the stream of cold gas can be heated after exiting from the hose by channeling it via a heat register and electrically heating it to the desired outlet temperature.

Devices are used for the cryotherapy of rheumatic diseases which produce a cold treatment gas of nitrogen and air in which device liquid nitrogen is vaporized by heat exchange with air, whereupon both media are mixed with one another. These devices are designed for carrying out many treatments per day in hospitals and therapy centers. They are accordingly expensive, for example, with regard to the removal of moisture and the warning apparatus for lack of oxygen in the case of unexpected total vaporization of the liquid nitrogen. In order to reduce this expense for devices which are intended only for occasional treatments in medical practice, the vessel 4 for the storage of the liquid nitrogen is made so small that it can hold, at the most, liquid nitrogen for a few individual treatments. The air is fed by a blower 1 with a dryer 2 and is partially channeled for nitrogen vaporization by means of the heat exchanging apparatuses 3 in the vessel 4 and partially mixed with the vaporized nitrogen and the previously diverted air a the blending intersection 6. The entire apparatus is preferably installed firmly on a cart 8.

What is claimed is:

1. In a device for producing a cold treatment gas from nitrogen and air for the cryotherapy of rheumatic diseases, according to which liquid nitrogen vaporizes and is mixed in the desired ratio with the dry air which is at a higher pressure, the improvement being a vessel for the storage of the liquid nitrogen and having a capacity for carrying out at least one treatment, a blower having a dryer for supplying air under high pressure, a blending intersection comprising an inlet pipe communicating with a first and a second branch conduits, said branch conduits being joined together to form an outlet pipe, said inlet pipe communicating with said blower for feeding air through said inlet pipe and into said branch conduits, said second branch conduit extending into said vessel and comprising a heat exchanger in said vessel with cooled air flowing there through, and said vessel being in flow communication with said outlet pipe whereby vaporized nitrogen is blended with cooled air and non-cooled air.

2. Device according to claim 1, characterized therein that said second branch conduit comprises a first tube extending from said inlet pipe and into said vessel and also extending out of said vessel, a second tube communicating with said vessel whereby vaporized nitrogen may flow therein, said second tube merging into said outlet pipe, and said first tube being telescoped into said second tube whereby the cooled air from said first tube is discharged into said second tube.

3. Device according to claim 1, characterized by an adjustment mechanism regulated by the temperature of the treatment gas for metering the amount of air for said blending intersection and for said heat exchanging apparatus.

4. Device according to claim 3, characterized therein that said blower and said vessel are firmly attached onto a cart.

5. Device according to claim 4, characterized therein that said adjustment mechanism is a damper.

6. Device according to claim 5, characterized therein that said heat exchanging apparatus is a pipe.

7. Device according to claim 3, characterized therein that said adjustment mechanism is a damper.

8. Device according to claim 1, characterized therein that connected to said blending intersection is an electrical heat adjusting means for the adjustment of the temperature of the cold treatment gas.

9. Device according to claim 1, characterized therein that said blower and said vessel are firmly attached onto a cart.

10. Device according to claim 1, characterized therein that said heat exchanging apparatus is a pipe.

* * * * *